United States Patent [19]

Mirviss et al.

[11] Patent Number: 4,786,740

[45] Date of Patent: Nov. 22, 1988

[54] WORK-UP OF DIALKYL PHOSPHORODITHIOIC ACID ESTERS

[75] Inventors: Stanley B. Mirviss, Stamford, Conn.; Claudia H. Elkins, White Plains, N.Y.; Sandra L. Urquhart, Wallington, N.J.

[73] Assignee: Stauffer Chemical Co., Westport, Conn.

[21] Appl. No.: 934,076

[22] Filed: Nov. 24, 1986

[51] Int. Cl.⁴ .............................................. C07F 9/165
[52] U.S. Cl. ..................................................... 549/221
[58] Field of Search .......................................... 549/221

[56] References Cited

U.S. PATENT DOCUMENTS

| | | | |
|---|---|---|---|
| 2,725,328 | 11/1955 | Diveley et al. | 549/221 X |
| 2,815,350 | 12/1957 | Speck | 549/221 X |
| 2,864,826 | 12/1958 | Diveley et al. | 549/221 X |
| 2,955,116 | 10/1960 | Diveley et al. | 549/221 |
| 4,282,153 | 8/1981 | Minn | 549/221 |
| 4,283,335 | 8/1981 | Minn | 549/221 X |
| 4,283,338 | 8/1981 | Minn | 549/221 X |

OTHER PUBLICATIONS

Diveley et al., J. Am. Chem. Soc., vol. 81 (1959) pp. 139-144.

*Primary Examiner*—Richard L. Raymond
*Attorney, Agent, or Firm*—Hensley M. Flash; Michael J. Bradley

[57] ABSTRACT

A process for purifying a reaction mixture comprising a phosphorodithioic acid ester of dichloro-para-dioxane prepared by reacting an O,O-dialkyl phosphorodithioic acid with a dichloro-para-dioxane in the presence of a catalytic amount of a Lewis acid. This process comprises washing the reaction mixture with an ammonium hydroxide solution, and preferably with an ammonium hydroxide solution containing ammonium chloride.

9 Claims, No Drawings

WORK-UP OF DIALKYL PHOSPHORODITHIOIC ACID ESTERS

BACKGROUND OF THE INVENTION

1. Field of the Invention

This invention relates to an improved process for the purification of dialkyl phosphorodithioic acid esters, and more specifically relates to the purification of a reaction mixture resulting from the reaction of an O,O-dialkyl phosphorodithioic acid and an organic chloride.

2. Related Information

U.S. Pat. No. 2,725,828 to Diveley et al. discloses that certain esters of dithiophosphoric acid have excellent insecticidal properties and can be prepaed by the substitution reaction of an O,O-dialkyl dithiophosphoric acid with a dichlorodioxane. This patent further discloses that the resulting product was purified by washing sequentially with water, dilute sodium hydroxide and then with water.

An article entitled "Two Organophosphorus Derivatives of p-Dioxane with Insecticidal and Acaricidal Activity" by W. R. Diveley, A. H. Haubein, A. D. Lohr and P. B. Moseley, J. Am. Chem. Soc. 81, pp. 139–144 (1959) discloses the preparation of 2,3-para-dioxanedithiol S,S-bis(O,O-diethyl phosphorodithioate)(dioxathion) from 2,3-dichloro-paradioxane and the appropriate O,O-dialkyl hydrogen phosphorodithioates in the presence of molecular equivalents of certain bases or catalytic quantities of certain catalysts, or from para-dioxene and bis-(dialkoxyphosphinothioyl) disulfide in the presence of catalytic quantities of iodine. In one of these processes, the resulting salt was removed by filtration and the filtrate washed with 5% sodium hydroxide twice with 15% brine. In another of these processes the reaction mixture was worked up by washing with 1% hydrochloric acid in 15% brine, and then neutralized with 10% sodium hydroxide using phenolphthalein indicator.

U.S. Pat. No. 2,815,850 (Speck, Dec. 3, 1957) discloses the use of a metal chloride from the group consisting of zinc chloride, ferrous chloride and stannous chloride to catalyze the reaction between O,O-dialkyl dithiophosphoric acids and chloro-organic compounds wherein a chlorine is replaced by an ortho,ortho-dialkyl dithiophosphoric acid radical. The reaction products were purified by sequentially washing the reaction mixture with water, sufficient aqueous sodium hydroxide to neutralize the acids present, and finally with fresh water.

U.S. Pat. No. 4,283,885 (Minn, Aug. 11, 1981) discloses a process for improving the yield of dialkyl dithiophosphoric acid esters produced by the Lewis acid catalyzed reaction of an O,O-dialkyl dithiophosphoric acid and an organic chloride. More specifically, the method discloses the improvement wherein the reaction is carried out in the presence of an anhydride of a fatty acid containing 2–5 carbon atoms. It was noted that the purity of the ester end-product could be improved by conducting the reaction in the presence of specified amounts of certain carboxylic acid anhydrides. The reaction mixture was washed with an acidic brine solution and then with dilute caustic to further purify the reaction mixture.

U.S. Pat. No. 4,283,338 (Minn, Aug. 11, 1981) discloses a method for improving the yield of dialkyl dithiophosphoric acid esters produced by the Lewis acid catalyzed reaction of an O,O-dialkyl dithiophosphoric acid and an organic chloride. More specifically, the process discloses the improvement wherein the reaction is conducted under sufficient pressure to maintain the liberated hydrogen chloride in the reaction system during the course of the reaction. The reaction mixture was purified by washing with brine and then dilute alkali.

U.S. Pat. No. 4,282,153 (Minn, Aug. 4, 1981) discloses a method for improving the yield of insecticidal compositions produced by reacting an O,O-dialkyl dithiophosphoric acid with a chloro-para-dioxane in the presence of a Lewis acid catalyst and a stoichiometric excess of the acid reactant. More specifically, the process discloses the improvement wherein certain bicyclo-heptenes are added to the system resulting from the reaction and reacted with the excess of O,O-dialkyl dithiophosphoric acid present in the system. In this process the final reaction mixture was also washed with an acidic salt solution of hydrochloric acid and sodium chloride and then with aqueous sodium hydroxide for further purification.

SUMMARY OF THE INVENTION

An object of this invention is to provide a process for removing the organochloro compound impurities that are the reaction products in the preparation of, for example, dioxathion. These organochloride impurities are undesirable because of possible mammalian toxicity or phytotoxicity. A further object of this invention is to remove undesirable excess raw materials.

Other objects and advantages of the present invention are described elsewhere within this specification.

This invention is a process for purifying a reaction mixture comprising a phosphorodithioic acid ester of dichloro-para-dioxane prepared by reacting an O,O-dialkyl phosphorodithioic acid with a dichloro-para-dioxane in the presence of a catalytic amount of a Lewis acid which comprises washing the reaction mixture with an ammonium hydroxide solution. This ammonium hydroxide solution can also contain ammonium chloride. The process can also take place in the presence of an inert organic solvent. A preferred dichloro-para-dioxane is 2,3-dichloro-para-dioxane and a preferred ortho,ortho-dialkyl phosphorodithioic acid is O,O-diethyl phosphorodithioic acid.

DETAILED DESCRIPTION OF THE INVENTION

The preparation of phosphorodithioic acid ester of dichloro-para-dioxane is well known. However, the reaction by-products and excess unreacted reactants can create concern from a safety and an environmental point of view. Therefore, additional processing is needed to separate and recover excess reactants and by-products. This invention minimizes the additional processing required to separate and recover unreacted reactants and potentially deleterious by-products, advantages not heretofore realizable. The reaction mixture that is purified by the process of this invention comprises unreacted reactants, the phosphorodithioic acid ester end-product and other reaction by-products.

The process of this invention is applicable to any O,O-dialkyl phosphorodithioic acid reactant and is particularly applicable where the alkyl groups are those having 1–4 carbon atoms because of the utility of the resulting products as insecticides. Where the alkyl groups are ethyl is also preferred because of the resulting usefulness of the end-product. However, the nature of the alkyl group is not critical with respect to the present process, and the invention is not limited to any particular alkyl groups.

The dichloro-para-dioxane useful in the present invention includes both the 2,3 and the 2,5-dichoroparadioxane with the 2,3 being especially preferred because of the utility of the resulting end-product.

The reactants are combined in the presence of a catalytic amount of a Lewis acid. Preferred catalysts are chlorides of zinc, iron and tin. Zinc and tin chlorides are preferred because they yield lighter colored products. It is noted that while the catalysts are referred to as chlorides, it is understood that metals or salts which are converted under the reaction conditions into the metal chlorides can be used as equivalents because of the nature of the reaction, and it is not intended that the process should be limited to one in which the metal chloride is added as such to the reaction mixture. The amount of catalyst used in the process of the present invention is not critical. However, a catalytic amount can range from about 0.05% to 2 mole percent based on the ortho,ortho-dialkyl phosphorodithioic acid reactant.

The reaction temperature can be any temperature at which the reaction takes place, but below the decomposition temperature of the product or any intermediates produced in the process. Temperatures ranging from about 40° to about 110° C. can be used.

The reaction is preferably carried out in a solvent which is inert in the reaction. However, solvents are not necessary. When a solvent is used, volatile aromatic hydrocarbons such as benzene, toluene, xylenes, chlorobenzenes, cymene, cycloaliphatic volatile hydrocarbons such as cyclopentane or cyclohexane and other solvents such as carbon tetrachloride, ethylene dichloride an perchloro ethylene are preferred because the reaction mixture exhibits good solubility in them and, further, the hydrogen chloride produced is not highly soluble in these solvents and, therefore, is readily removed after the reaction is completed by distillation.

Following completion of the reaction, the reaction mixture is conventionally purified by the following steps. The reaction mixture is usually sequentially washed with water, brine, and sufficient sodium hydroxide to neutralize excess acid present. The brine can be an acidic combination of HCl and sodium chloride.

Surprisingly and unexpectedly, it has been discovered that if the reaction mixture is mixed with an ammonium hydroxide solution instead of the typical sodium hydroxide used to neutralize excess acid, the resulting impurities are substantially reduced, i.e., both unreacted reactants and by-products of the reaction.

During the washing process, an emulsion can be formed which is difficult to break or otherwise require a standing time for complete separation. It has been found that if ammonium chloride is included in the ammonium hydroxide solution, an emulsion will either not form or at least will separate quickly.

It is believed that unreacted O,O-dialkyl phosphorodithioic acid reacts with the ammonium hydroxide to form ammonium salts. Additionally, O,O-dialkyl phosphorodithioic acid reacts with the hydrogen chloride produced by the reaction to form dialkyl phosphorochloridothionate. Trichlorodioxanes can also be impurities present in the dichloro-para-dioxane reactant. Additionally, various impurities can be present in the dialkyl phosphorodithioic acid reactant, e.g. compounds of the formula

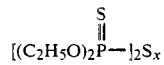

wherein x equals 2 and higher, i.e. diethyl phosphorothiono polythionates.

In the reaction of the O,O-dialkyl phosphorodithioic acid with the dichloro-para-dioxane, it is preferred that the O,O-dialkyl phosphorodithioic acid be in stoichiometric excess. This stoichiometric excess can generally range from about 0.01 mole to about 10 moles per mole of the dichloropara-dioxane, with a range from about 0.1 mole to about 2.0 moles being preferred. When the resulting reaction mixture is washed with ammonium hydroxide solution, it is preferred that the ammonium hydroxide solution be in stoichiometric excess over the amount of O,O-dialkyl phosphorodithioic acid used, and in particular a molar excess ranging from about 2 moles to about 20 moles of ammonium hydroxide per mole of excess O,O-dialkyl phosphorodithioic acid is preferred, with a range of from about 3 moles to about 12 moles of ammonium hydroxide per mole of excess O,O-dialkyl phosphorodithioic acid being particularly preferred.

After the reaction of the O,O-dialkyl phosphorodithioic acid and the dichloro-para-dioxane, the reaction mixture can usually be washed with an acidic brine solution, i.e. HCl and saturated sodium chloride, prior to the washing of the reaction mixture with the ammonium hydroxide solution. The typical washing with a sodium hydroxide solution can be excluded prior to the washing with the ammonium hydroxide solution.

When a solvent is used in the course of this reaction, the end-product can be separated by following conventional distillation procedures.

The following experiments describe various embodiments of this invention. Other embodiments will be apparent to one of ordinary skill in the art from a consideration of this specification or practice of the invention disclosed herein. It is intended that the specifications and experiments be considered as exemplary only, with the true scope and spirit of the invention being indicated by the claims which follow the experiments.

EXPERIMENT 1

A reaction flask was charged with 170.7 grams of technical grade 2,3-dichloro-para-dioxane (DCD, 1.00 mole on a 92 weight percent purity basis), 494.5 grams of O,O-diethyl phosphorodithioic acid (DEPTA, 2.18 moles on a 82 weight percent purity (gas chromatography, gc) basis), 600 grams of toluene and 1.6 grams of anhydrous zinc chloride. The reaction mixture was heated with stirring to 50° C. and held for 2 hours. The temperature was then raised to 60° C. and held for 80 minutes. The resulting reaction mixture was cooled and the contents divided into parts for comparative workup (washing) studies. Each 303.5 grams part was now washed with a combined solution of 75 milliliters of 2 weight percent HCl and 25 milliliters of saturated NaCl.

Batch A

The diluted HCl/NaCl washed dioxathion endproduct was further washed with 150 milliliters of 10 weight percent NaOH. Layers were separated after 15 minutes. The organic layer was again washed with 150 milliliters of 10 weight percent NaOH. Layers were separated after 20 minutes. The washed organic layer was then vacuum stripped, first at 15 mm.Hg up to 60°

C. and then under high vacuum (0.1–0.5 mm.Hg) at up to 75° C. The residue was analyzed by liquid chromatography (lc) and gc with the results tabulated below.

Batch B

The procedure of Batch A was followed except that 60 milliliters of 25 weight percent NaOH was used for each of two washes.

Batch C

Again, the procedure of Batch A was followed except that 25 milliliters of 15 N NH$_4$OH was used for each of two washes. The second wash produced a strong emulsion which took about 1 hour to show any separation and 12 hours for complete separation.

Batch D

The same procedure as in Batch A was followed except that 50 milliliters of 7.5 N NH$_4$OH was used for each of two washes. The second wash produced an emulsion which separated completely after 12 hours.

Batch E

The procedure of Batch A was followed except that 75 milliliters of 5N NH$_4$OH was used for each of two washes. Again, the second wash produced an emulsion which took several hours for complete separation.

Batch F

The procedure of Batch D was followed except that 50 milliliters of 7.5 N NH$_4$OH containing 10 grams of dissolved NH$_4$Cl was used for the washes and the layer separation of the first wash was completed in a few minutes. In the second wash, an emulsion did not form.

TABLE I
RESULTS OF COMPARATIVE WASHING STUDIES

| Batch | [1]DEPCT Wt. % | [2][(EtO)$_2$P(S)]$_2$S$_x$ Wt. % | [3]DCD Wt. % |
|---|---|---|---|
| A | 0.14 | 1.1 | 0.67 |
| B | 0.21 | 0.5 | 0.97 |
| C | none | none | 0.37 |
| D | none | none | 0.42 |
| E | trace | 0.1 | 0.25 |
| F | trace | none | 0.10 |

| Batch | [4]Cl$_3$ Dioxane Wt. % | [5][(EtO)$_2$P(S)]$_2$S Wt. % |
|---|---|---|
| A | 0.3 | 2.8 |
| B | 0.3 | 2.9 |
| C | 0.2 | 0.1 |
| D | 0.2 | 0.6 |
| E | 0.2 | 1.9 |
| F | 0.1 | 1.8 |

[1]diethyl phosphorochloridothionate
[2]diethyl phosphorothiono polythionate
[3]2,3-dichloro-para-dioxane
[4]trichlorodioxane
[5]bis-(diethyl phosphorothiono) sulfide

What is claimed is:

1. A process for purifying a reaction mixture comprising a phosphorodithioic acid ester of dichloro-para-dioxane prepared by reacting an 0,0-dialkyl phosphorodithioic acid with a dichloro-para-dioxane in the presence of a catalytic amount of a Lewis acid which comprises washing the reaction mixture with an ammonium hydroxide solution.

2. The process of claim 1 wherein the ammonium hydroxide solution contains ammonium chloride.

3. The process of claim 1 wherein the reaction mixture further comprises an inert organic solvent.

4. The process of claim 1 wherein the dichloro-para-dioxane is 2,3-dichloro-para-dioxane.

5. The process of claim 1 wherein the 0,0-dialkyl phosphorodithioic acid is 0,0-diethyl phosphorodithioic acid.

6. The process of claim 5 wherein the dichloro-para-dioxane is 2,8-dichloro-para-dioxane.

7. The process of claim 6 wherein the reaction mixture further comprises an inert organic solvent.

8. The process of claim 7 wherein the ammonium hydroxide solution contains ammonium chloride.

9. The process of claim 8 wherein the 0,0-diethyl phosphorodithioic acid is in stoichiometric excess over the 2,3-dichloro-para-dioxane and the ammonium hydroxide solution is in stoichiometric excess over the 0,0-diethyl phosphorodithioic acid.

* * * * *

UNITED STATES PATENT AND TRADEMARK OFFICE
CERTIFICATE OF CORRECTION

PATENT NO. : 4,786,740

DATED : November 22, 1988

INVENTOR(S) : Stanley B. Mirviss et al.

It is certified that error appears in the above-identified patent and that said Letters Patent is hereby corrected as shown below:

In Col. 1, at line 13, the number "2,725,828" should be --- 2,725,328 ---;
at line 40, the number "2,815,850" should be --- 2,815,350 ---;
at line 51, the number "4,283,885" should be --- 4,283,335 ---.

In col. 4, at line 54 the number "80" should be --- 30 ---.

In Claim 6, the last word should be --- 2,3-dichloro-para-dioxane ---

Signed and Sealed this

Seventeenth Day of April, 1990

Attest:

HARRY F. MANBECK, JR.

Attesting Officer

Commissioner of Patents and Trademarks